(12) United States Patent
Nevshupa et al.

(10) Patent No.: US 8,789,430 B2
(45) Date of Patent: Jul. 29, 2014

(54) FORCE MEASURING DEVICE (75) Inventors: Roman Nevshupa, Guipúzcoa (ES);
Marcello Conte, Guipúzcoa (ES);
Andoni Delgado Castillo, Guipúzcoa (ES); Amaya Igartua Aranzabal, Guipúzcoa (ES); Fernando Egaña Farizo, Guipúzcoa (ES); Ana Aranzabe Garcia, Guipúzcoa (ES)

(73) Assignee: Fundacion Tekniker, Guipuzcoa (ES)

( * ) Notice: Subject to any disclaimer, the term of this patent is extended or adjusted under 35 U.S.C. 154(b) by 131 days.

(21) Appl. No.: 13/520,109

(22) PCT Filed: Dec. 29, 2009

(86) PCT No.: PCT/ES2009/070635
§ 371 (c)(1),
(2), (4) Date: Jul. 26, 2012

(87) PCT Pub. No.: WO2011/080355
PCT Pub. Date: Jul. 7, 2011

(65) Prior Publication Data
US 2012/0279321 A1 Nov. 8, 2012

(51) Int. Cl.
*G01L 1/00* (2006.01)
*G01L 5/00* (2006.01)

(52) U.S. Cl.
USPC ............................... 73/862.541; 73/862.381

(58) Field of Classification Search
USPC ...................................... 73/862.541, 862.381
See application file for complete search history.

(56) References Cited

U.S. PATENT DOCUMENTS

| 5,115,664 A | 5/1992 | Hegde et al. |
| 5,212,657 A | 5/1993 | Uchikawa et al. |

(Continued)

FOREIGN PATENT DOCUMENTS

| GB | 1 214 864 A | 12/1970 |
| JP | 2000 074817 A | 3/2000 |
| WO | WO 03/060487 A1 | 7/2003 |

OTHER PUBLICATIONS

Liu, H. and Bhushan, B., "Adhesion and friction studies of microelectromechanical systems/nanoelectromechanical systems materials using a novel microtriboapparatus", Journal of Vacuum Science and Technology A, 2003, vol. 21, No. 4, pp. 1528-1538.

(Continued)

*Primary Examiner* — Lisa Caputo
*Assistant Examiner* — Jamel Williams
(74) *Attorney, Agent, or Firm* — Florek & Endres PLLC (57) ABSTRACT

The invention consists of a measurement device for measuring the force applied by a contact member on the surface of a sample, comprising a vacuum or controlled atmosphere chamber in which there are housed the sample and the contact member, mechanical means for transmitting the force exerted by the contact member in the form of the displacement of one or several flexible members and one or several sensors suitable for measuring said displacement. The device comprises motor-driven linear micropositioners incorporated inside the vacuum or controlled atmosphere chamber for positioning sensor(s). As a result of the system, it is not necessary to break the vacuum to calibrate the sensors, saving time and facilitating the measurement.

4 Claims, 4 Drawing Sheets

(56) References Cited

U.S. PATENT DOCUMENTS

| | | | | |
|---|---|---|---|---|
| 6,094,967 | A * | 8/2000 | Cavdar | 73/9 |
| 6,981,400 | B1 * | 1/2006 | Sowell et al. | 73/9 |
| 7,000,451 | B1 * | 2/2006 | Wegand et al. | 73/9 |
| 8,161,803 | B2 * | 4/2012 | Oh et al. | 73/81 |
| 2011/0265559 | A1 * | 11/2011 | Oh et al. | 73/81 |
| 2013/0098139 | A1 * | 4/2013 | Adams, Jr. | 73/7 |
| 2013/0098145 | A1 * | 4/2013 | Oh et al. | 73/81 |

OTHER PUBLICATIONS

Stachowiak, G.W. et al., "Measurement of Friction and Wear", Tribology Series, 2004, vol. 44, pp. 81-83.

International Search Report issued by the International Searching Authority (ISA/O.E.P.M.) on Sep. 20, 2010 in connection with International Application No. PCT/ES2009/070635.

* cited by examiner

FORCE MEASURING DEVICE

This application is a §371 national stage application of PCT International Application No. PCT/ES2009/070635, filed Dec. 29, 2009, the contents of all of which are hereby incorporated by reference into this application.

FIELD OF THE INVENTION

The present invention applies to the field of the tribology. More specifically, it relates to a device for measuring the force exerted in one or two directions on a surface to be studied.

BACKGROUND OF THE INVENTION

There are currently different techniques for characterizing mechanical, tribological, physicochemical or other properties of materials, surface coatings and lubricants, which use some form of controlled mechanical action on the surface to be characterized in a special atmosphere, for example, in ultra-high vacuum or in an atmosphere of controlled gas and pressure. In these techniques, a burin or punch which exerts a pressure force in the direction normal to the surface to be characterized is normally used. Also, in some cases as the result of the traction of the burin or punch on the surface to be characterized a friction force is produced in the direction tangential to the surface to be characterized. The control of the normal force and the measurement of the tangential force with high precision and reproducibility are conditions necessary for many characterization techniques. Furthermore, to characterize different materials such as ceramics, metals, metal alloys, polymers, composite materials, hard surface coatings, solid or liquid lubricants, greases, etc., which have very different mechanical properties such as hardness, modulus of elasticity, free surface energy, etc., the device has to have a broad range of measurement.

There are several indirect methods and devices for measuring forces described in U.S. Pat. No. 5,115,664, U.S. Pat. No. 5,212,657, U.S. Pat. No. 7,000,451, in Stachowiak G. Experimental Methods in Tribology.—Amsterdam: Elsevier, 2004; and in Liu H. Bhushan B. Adhesion and friction studies of microelectromechanical systems/nanoelectromechanical systems materials using a novel microtriboapparatus. J. Vac. Sci. Technol. A21(4), 2003, pp. 1528-1538. These methods use a flexible member with a well determined stiffness constant. This flexible member is usually located between a stiff base and the sample or between a stiff base and the punch or burin which exerts force on the sample. The normal force exerted by the burin or punch on a surface is determined by the deflection of the flexible member in the direction normal to the surface of the sample. The tangential force resulting from the friction between the burin or punch and the surface to be characterized is determined by the deflection of the flexible member in the direction tangential to the surface. In both cases it is necessary to determine the stiffness constants of the flexible member in every direction by means of prior calibration of a sensor.

In the devices described in the previously mentioned patents and publications, the deflection of the flexible member is measured by means of a sensor, which by way of illustration can be one of the following types: fiber optic, capacitive, inductive, laser interferometric sensor or the like. One of the most widely used ones is the fiber optic sensor. In the mentioned devices, the distance between the sensor and the flexible member is pre-established before creating the vacuum or controlled atmosphere and cannot be changed or adjusted without breaking the vacuum. In that of the publication of Liu H., Bhushan B. Adhesion and friction Studies of microelectromechanical systems/nanoelectromechanical systems materials using a novel microtriboapparatus. J. Vac. Sci. Technol. A21(4), 2003, pp. 1528-1538, a fiber optic sensor is used in which the distance between the end of an optical fiber and a reflective surface can be adjusted by means of a manually operated external micropositioner. This external micropositioner allows selecting a near range or a far range, depending on the necessary measurement resolution. In this device there are two piezoelectric motors used for moving the sample in two coordinates. However, these piezoelectric motors are not used for the movement and adjustment of the fiber optic sensors.

The manual adjustment of the position of the sensors by means of an external positioner is a common feature of all previously disclosed devices and constitutes a significant obstacle when performing the fine adjustment of the position of the sensor or calibrating it again in vacuum or controlled atmosphere applications when, in order to perform this adjustment or calibration, it is necessary to break the vacuum or controlled atmosphere. In these applications it is not possible to adjust the position or calibrate the sensors used for measuring the deflection of the flexible members remotely. In ultra-high vacuum systems which require heating of the system for the degassing thereof at a temperature normally comprised between 100° C. and 400° C., deformations of the structural members of the system may occur as the result of the high temperature or the pressure. This can affect the position of the sensors installed within the system, cause their misalignment, be detrimental to the measurement and, in some cases, prevent their use for measuring forces. In existing systems, in order to adjust the position of the sensors again it is necessary to open the system and break the vacuum or the controlled atmosphere, which entails losses of time (up to several days) and considerable economic costs.

OBJECT OF THE INVENTION

The object of the invention is to palliate the technical problems mentioned in the previous section. To that end, it proposes a measurement device for measuring the force applied by a contact member on the surface of a sample, comprising a vacuum or controlled atmosphere chamber in which there are housed the sample and the contact member, mechanical means for transmitting the force exerted by the contact member in the form of the displacement of at least one flexible member and at least one sensor suitable for measuring said displacement and furthermore comprising at least one motor-driven linear micropositioner incorporated inside the vacuum or controlled atmosphere chamber for positioning an associated sensor. The device preferably comprises a control system for each micropositioner located outside the vacuum or controlled atmosphere chamber for controlling the movement of the sensor remotely. The device is suitable for measuring a force that is tangential or normal to the surface or both forces at the same time. The sensors are optionally optic sensors. There is preferably a microactuator capable of operating the micropositioner and the latter is located in linear guides.

BRIEF DESCRIPTION OF THE DRAWINGS

For the purpose of aiding to better understand the features of the invention according to a preferred practical embodiment thereof, a set of drawings is attached to the following description in which the following is depicted with an illustrative and non-limiting character.

DETAILED DESCRIPTION OF THE INVENTION

Figure 1:
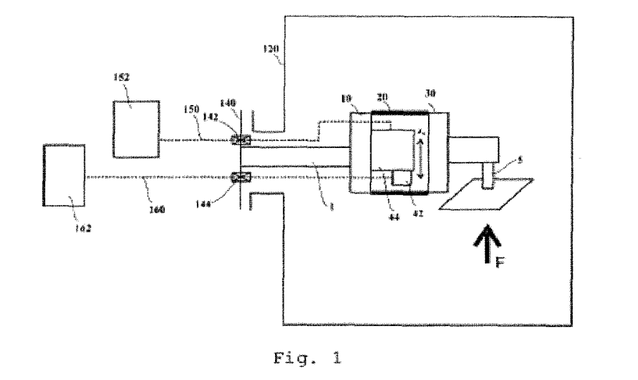
FIG. 1 shows a schematic view of the device of the invention for measuring a single force.

The invention consists of using one or several motor-driven linear micropositioners incorporated in the force measurement device and located inside the vacuum chamber. The device (FIG. 1) has a stiff base 1 connected to the vacuum or controlled atmosphere chamber 120, a support 10 connected to the stiff base 1, and at least to another support 30 connected to a support of the burin or punch 5, one or several flexible members 20 connected between the supports 10 and 30. The force F exerted between the burin or punch 5 and the surface is transmitted by the mechanical means to the flexible members 20, causing their deformation and the deflection $z_0$ of the end of the flexible member connected to the support 30 with respect to the support 10. The amount of movement of the flexible member is measured by means of a sensor 42 which, by way of illustration, can be one of the following types: fiber optic, capacitive, inductive, laser interferometric sensor or the like. The power supply and measurement system 162 of the sensor is normally located outside the vacuum or controlled atmosphere chamber and is connected to the sensor by means of corresponding means for the transmission of the signal (electric cables, optical fibers, optical guides or the like) 160 and suitable wall sleeves 144 which allow supplying power to the sensor and measuring the deflection of the flexible member remotely and without needing to break the vacuum or controlled atmosphere. There is connected to the support 10 of the device a micropositioner 44 having one or several linear guides, a mobile carriage which is connected to one or several linear guides and can move along these linear guides by means of a microactuator which, by way of illustration and without limiting the scope of the invention, can be a mechanical, piezoelectric, magnetostrictive type microactuator, etc. The micropositioner is connected to the base of the device such that the linear guides are located parallel to the normal of the surface of the flexible member the deflection of which is measured. Each sensor is fixedly connected to the movable part (mobile carriage) of the micropositioner. The sensor connected to the mobile carriage can thus move towards or away from the surface of the flexible member the deflection of which is measured. The power supply and control of the movement of the sensor are performed through the control system 152 of the micropositioner located outside the vacuum or controlled atmosphere chamber. The system for the power supply and control of the micropositioners is connected to the micropositioners by means of the corresponding electric cables 150 and wall sleeves 142 which allow supplying power and controlling the micropositioners remotely and without needing to break the vacuum or controlled atmosphere, which offers considerable savings in measurement time and economic savings. The microactuator has to have positioning precision suited to the type of sensor used. The use of a linear micropositioner allows moving the sensor in the direction normal to the surface of the flexible member without its angular deviation, which is a necessary condition for maximum precision of the measurement.

When two forces in two different directions between the burin or punch and the surface, for example in the direction normal and tangential to the surface, are measured, two assemblies formed by supports 10 and 30, flexible members 20 and the sensor 42 are used. These assemblies are located inside the vacuum or controlled atmosphere chamber and are connected to one another such that the normal to the surface of the first assembly coincides with the direction of the first force to be measured and the normal to the surface of the second assembly coincides with the direction of the second force to be measured. The displacement of the flexible members of each assembly is measured by a corresponding sensor in the same manner as in the previously described case of the device for measuring a single force. A corresponding micropositioner incorporated in the device and located inside the vacuum or controlled atmosphere chamber is used to position each sensor. The control and power supply system of the micropositioners can be a single system for two micropositioners or independent for each micropositioner and is located outside the vacuum or controlled atmosphere chamber.

Device for Measuring a Single Force

The device for measuring a single force allows measuring the force exerted between the burin or punch and the solid surface in the direction normal or tangential to the surface. The device needs no modifications in its structure to measure either force, it must simply be placed and adjusted in a suitable manner with respect to the solid surface.

Figure 3:
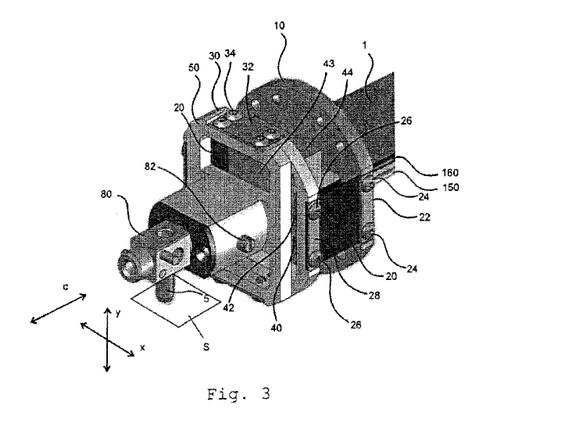
FIG. 3 shows an isometric view of the device for measuring a force in the direction tangential to the surface.

FIG. 3 shows the device for measuring a single force in the direction tangential to the surface. Two rectangular parallel leaf springs 20 form the flexible member of the force measurement device. The strips are connected in the opposite sides of the supports 10 and 30 symmetrically with respect to the longitudinal axis c and with its planes parallel to one another. Some ends of the strips are held to the support 10 by means of two plates 22 (one for each strip) and four screws 24 (two for each strip). Other ends of the strips are held to the support 30 by means of two plates 28 (one for each strip) and four screws 26 (two for each strip). The support 10 is assembled on a stiff base 1. The movable support 30 rigidly connects to the support 50 by means of eight screws 34 and two plates 32. In the center of the projecting part of the support 50 there is a cylindrical through hole the axis of which is parallel to axis c (FIG. 3). The cylindrical part of the support 80 is introduced in this hole. The support 80 is fixed to the support 50 with a set screw 82. The angular position of the assembly of the support 80 with the burin or punch 5 can thus be adjusted with respect to the surface in which the force to be measured is exerted. The burin or punch 5 is normally positioned with its longitudinal axis in the position normal to the surface (parallel to the x axis). The entire device is positioned with respect to the surface in which the force is exerted such that the normals of the planes of the strips 20 coincide with the direction in which the force is exerted.

When the force is applied to the burin or punch 5 in the tangential direction with respect to the surface (y axis), the device is positioned and fixed in the stiff base 1 with the normals of the planes of the strips 20 in the x direction.

Figure 7:
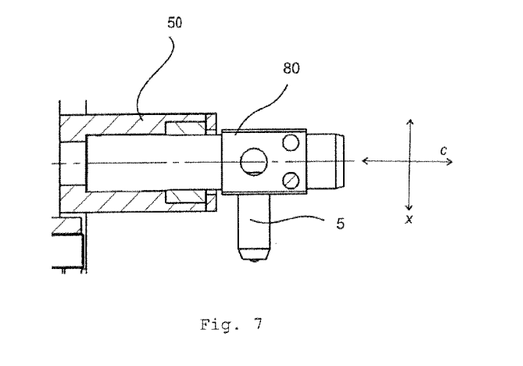
FIG. 7 shows a section of the support 50 with the support 80 and the burin or punch 5.

When the force is measured in the direction normal (x axis) to the surface, the device is positioned and fixed in the stiff base 1 such that the planes of the parallel strips are parallel to the solid surface in which the force is exerted by means of the burin or punch 5 (FIGS. 3 and 7).

Figure 4:
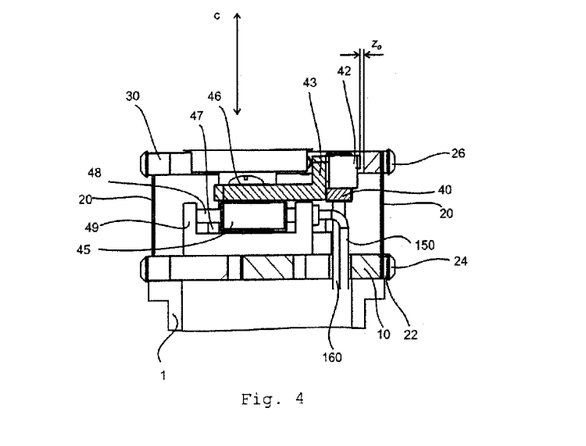
FIG. 4 shows a section of the device for measuring a force in the direction tangential to the surface.

When the force is exerted between the burin or punch 5 and the solid surface in the pre-selected direction (normal or tangential to the surface) depending on the orientation of the strips 20 with respect to the surface as previously described, the parallel leaf springs 20 connected with their ends between the supports 30 and 10, and being the members of lesser stiffness, are elastically deformed. The movement of support 30 with respect to support 10 which occurs due to the deformation of the parallel leaf springs 20 is measured using a sensor 42. FIG. 4 shows the design of the positioning device of the sensor. The sensor is located opposite the surface of the support 10 with the measuring surface of the sensor towards the surface of the support 10. The axis of the sensor 42 has to be in the position normal to the surface of the support 30 with a maximum angular deviation of usually 4 degrees or less. The sensor 42 is fixed on an L-shaped plate 43 with a clamp 40. The clamp 40 has a notch through which the electric cables or optical guides 160 of the sensor 42 pass. The plate 43 is assembled on the mobile carriage of the micropositioner 45 with screws 46. The micropositioner 44 (FIG. 1) normally comprises the base 49 (FIG. 4), one or several linear guides 48, a mobile part (mobile carriage) 45, a microactuator 47 and the means for the transmission of power supply and control signals 160. The mobile carriage of the micropositioner 45 is connected to the linear guides 48 connected fixedly to the base of the micropositioner 49. The microactuator 47 of the micropositioner allows moving the mobile carriage 45 together with the sensor 42 along the linear guides 48 and such that the sensor can move towards or away from the surface of the support 30 without changing its angular position. The range of linear movement usually ranges between several micrometers and several millimeters, depending on the features of the sensor used. The microactuator of the micropositioner can be, by way of illustration and without limiting the scope of the invention, can be a mechanical, piezoelectric, magnetostrictive type microactuator, etc., and has the positioning precision suited to the type of sensor used. By way of illustration and without limiting the scope of the invention, the precision of the micropositioner usually has to be equal to or less than one micrometer.

The force F is determined from the movement value $\Delta z$ measured with the sensor and a constant k, the value of which is determined by means of prior calibration, according to the following formula:

$$F = \Delta z k.$$

Figure 2:
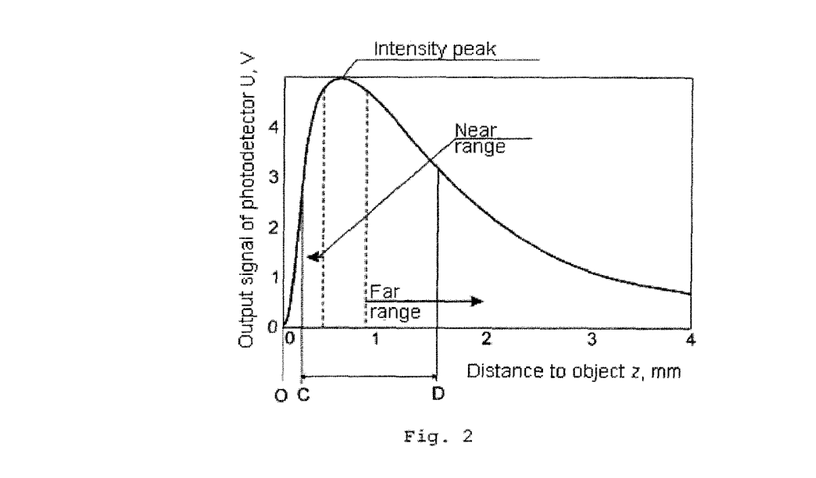
FIG. 2 shows a graph which depicts the signal of a photodetector as a function of the distance between the end of the guides of an optical sensor and the object. C and D are the nominal sensor positions in the near and far range, accordingly.

Before beginning the measurement of the force, the sensor is located by means of the micropositioner 45 in the initial measuring position of the sensor. When an optical sensor is used, the measurement can be performed in two ranges of measurement: the near range and the far range. Specifically, when the near range is chosen for the measurement, the optical sensor is located at the distance $z_0 = OC$ (FIG. 2) from the surface of the and of the flexible member connected to the support 30 or another surface of member 30 parallel to the end of the flexible member connected to the support 30, which in this case has to be reflective to light, used by the sensor, whereas when the far range is chosen, the optical sensor is located at the distance $z_0 = OD$ (FIG. 2) of the reflective surface of the support 30. During the measurement of force, the micropositioner maintains the sensor fixed with respect to the support 10.

When the measurement is performed in a controlled atmosphere or in the vacuum, the adjustment of the position of the sensor is done before or after creating the vacuum or controlled atmosphere. When the force measurement device is used in an ultra-high vacuum which requires heating the entire system for the degassing thereof, it is preferable to perform the adjustment of the position of the sensor after the heating so that the possible thermal deformations do not affect the adjustment of the position of the sensor. Furthermore, the micropositioner allows remotely changing the range of measurement between several tests without needing to break the vacuum or controlled atmosphere, which offers more advanced measurement flexibility and reproducibility and the broadest range of measurement with respect to existing devices. For their use in a vacuum, all the mechanical members of the device are made from materials with a low rate of desorption and emission of gases. Furthermore, for their use in an ultra-high vacuum, these materials have to allow heating up to 150° C. For example, by way of illustration and without limiting the scope of the invention, the materials for manufacturing the components of the device belong to the following group: stainless steel, copper and copper alloys, titanium and titanium alloys, aluminum and aluminum alloys, etc. The sensor and the micropositioner also have to be suitable for their use in a vacuum. The design of the device allows quickly removing the gases from the inside thereof, which allows its use in an ultra-high vacuum.

Device for the Simultaneous Measurement of Two Forces

Figure 5:
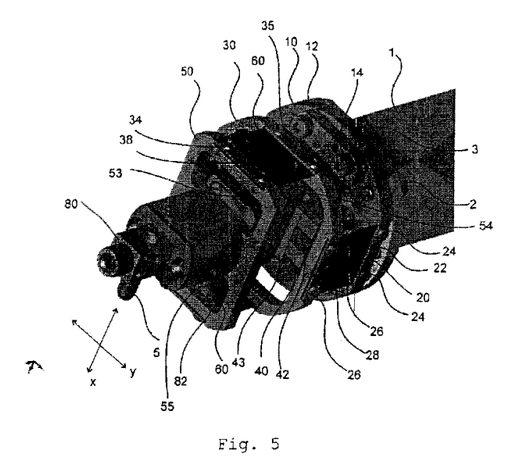
FIG. 5 shows an isometric view of the device for measuring two forces.

The device for the simultaneous measurement of two forces in two perpendicular directions (x and y axes) is presented in FIG. 5. The device consists of supports 10, 30 and 50 to which there are connected two pairs of flexible members in the form of parallel strips 20 and 60. The strips 20 are parallel to one another in the opposite sides of the supports 10 and 30 and symmetrically with respect to the c axis. The strips 60 are parallel to one another in the opposite sides of the supports 30 and 50 with the strips parallel to one another and symmetrically with respect to the axis c. The parallel strips 20 are connected on one side to the fixed support 10 by means of two plates 22 (one for each strip) and four screws 24 (two for each strip) and on the other side to the support 30 with two plates 28 (one for each strip) and four screws 26 (two for each strip). A second pair of parallel strips 60 is connected on one side to the support 30 with two plates 35 (one for each strip) and four screws 34 (two for each strip) and on the other side to the support 50 with two plates 38 (one for each strip) and four screws 34 (two for each strip). The strips 20 are in the position perpendicular to the strips 60. In the projecting part of the support 50 there is a cylindrical through hole in which the cylindrical part of the support 80 is introduced and is fixed with a set screw 82. The burin or punch 5 which is used to exert the forces in the normal and/or tangential direction with respect to the solid surface is located in the support 80. The position of the assembly of the support 80 and the burin or punch 5 is adjusted such that the longitudinal axis of the burin or punch 5 coincides with the normal of the solid surface on which the forces are exerted. The entire device is adjusted and fixed to the stiff base 1 such that the normal of the strips 20 coincides with the tangent of the solid surface on which the forces are exerted and the normal of the strips 60 coincides with the normal of the same solid surface. The adjustment and fixing of the position of the device is carried out with the screws 2 and 3.

The operation of the device for measuring two forces is similar to that of measuring one force.

Figure 8:
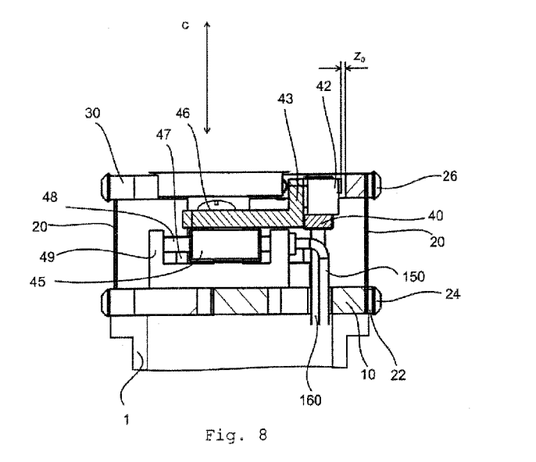
FIG. 8 shows a section of the device for measuring the force in the direction tangential to the surface forming part of the device for measuring two forces.

When a force tangential to the surface is exerted between the burin or punch 5 and the solid surface, the support 30 together with the strips 60, supports 50 and 80 move along the y axis parallel to their initial position. The movement of the support 30 is measured using a sensor, in this case an optical sensor 42. FIG. 8 shows the design of the device for measuring the force in the direction tangential to the surface which forms part of the device for measuring two forces. This part of the device is identical to the device for positioning the sensor in the case when a single force in the direction tangential to the surface is measured. The sensor is located opposite the surface of the support 30 with the measuring surface of the sensor towards the surface of the support 30. The axis of the sensor 42 has to be in the position normal to the surface of the support 30 with a maximum angular deviation usually of 4 degrees or less. The plate 43 is assembled on the mobile carriage of the micropositioner 45 with screws 46. The mobile carriage of the micropositioner 45 is connected to the linear guides 48, which are in turn fixedly connected to the base of the micropositioner 49. The microactuator 47 of the micropositioner allows moving the mobile carriage 45 together with the sensor 42 along the linear guides 48 such that it can move the sensor towards or away from the surface of the support 30 without changing its angular position. The range of linear movement usually ranges between several micrometers and several millimeters depending on the characteristics of the optical sensor used. The microactuator of the micropositioner can be, by way of illustration and without limiting the scope of the invention, a mechanical, piezoelectric, magnetostrictive type microactuator, etc., and has the positioning precision suited to the type of sensor used. By way of illustration and without limiting the scope of the invention, the precision of the micropositioner usually has to be equal to or less than one micrometer.

Figure 6:
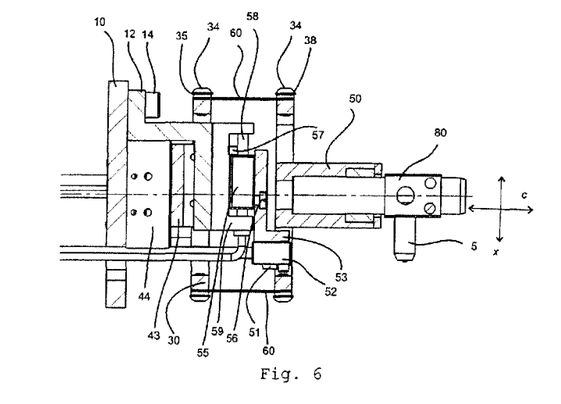
FIG. 6 shows a section of the device for measuring two forces.

When a force normal to the surface is exerted between the burin or punch 5 and the solid surface, the strips 60 are elastically deformed and support 50 together with support 80 moves along the x axis parallel to their initial position. In the case when two forces, the normal and the tangential, are exerted simultaneously, the movement of the components 50 and 80 along the x axis occurs independently of their movement along the y axis. The movement of the support 50 in the y direction is measured using a sensor 52. FIG. 6 shows the section of the device for measuring two forces. The sensor 52 is located opposite the surface of the support 50 with the measuring surface of the sensor towards the surface of the support 50. The axis of the sensor 52 has to be in the position normal to the surface of the support 30 with a maximum angular deviation usually of 4 degrees or less. The sensor is fixed on a plate 53 with a clamp 51. The plate 53 is assembled on the mobile carriage of the micropositioner 55 with screws 56. The mobile carriage of the micropositioner 55 is connected to the linear guides 58 fixedly connected to the base of the micropositioner 59. The microactuator 57 of the micropositioner allows moving the mobile carriage 55 together with the sensor 52 along the linear guides 58 such that it allows moving the sensor towards or away from the surface of the support 50 without changing its angular position. The range of linear movement usually ranges between several micrometers and several millimeters depending on the characteristics of the sensor used. The microactuator of the micropositioner can be, by way of illustration and without limiting the scope of the invention, a mechanical, piezoelectric, magnetostrictive type microactuator, etc., and has the positioning precision suited to the type of sensor used. By way of illustration and without limiting the scope of the invention, the precision of the micropositioner usually has to be equal to or less than one micrometer.

The micropositioner 54 is assembled on a Z-shaped support 12 which, where appropriate, is fixed to the support 10 with two screws 14. The micropositioner 54 is thus fixed with respect to the support 10.

Before beginning the measurement of the forces, the optical sensors 52 and 42 are located by means of the micropositioners 54 and 45 in their initial positions, corresponding to the ranges of measurement chosen for each sensor. Specifically, when the near range is chosen for the measurement, the optical sensor 45 or 54 is located at the distance $z_0$=OC (FIG. 2) from the reflective surface of the support 30 or 50, whereas when the far range is chosen, the optical sensor 45 or 54 is located at the distance $z_0$=OD (FIG. 2) from the reflective surface of the support 30 or 50, respectively. During the measurement of force, the micropositioners 45 and 54 maintain the optical sensors in the fixed position with respect to the support 10.

The force $F_T$ in the direction tangential to the surface is determined from the movement value $\Delta z_T$ of the support 30 measured with the sensor 42 and a constant $k_N$, the value of which is determined by means of the prior calibration of the strips 60, according to the following formula:

$$F_N = \Delta z_N k_N.$$

The force $F_N$ in the direction normal to the surface is determined from the movement value $\Delta z_N$ of the support 50 in the x direction measured with the sensor 52 and a constant $k_T$, the value of which is determined by means of the prior calibration of the strips 20, according to the following formula:

$$F_T = \Delta z_T k_T.$$

When the measurement is performed in a controlled atmosphere or in a vacuum, the adjustment of the position of one or two sensors is carried out before or after creating the vacuum or controlled atmosphere. When the force measuring device is used in an ultra-high vacuum which requires heating the entire system for the degassing thereof, it is preferable to perform the adjustment of the positions of the sensors after the heating so that the possible thermal deformations do not affect the adjustments of the positions of the sensors. Furthermore, the micropositioners allow remotely changing the range of measurement of one or two sensors between several tests without needing to break the vacuum or controlled atmosphere, which offers more advanced measurement flexibility and reproducibility and the broadest range of measurement with respect to existing devices. For their use in a vacuum, all the mechanical members of the device are made from materials with a low rate of desorption and emission of gases. Furthermore, for their use in an ultra-high vacuum, these materials have to allow heating up to 150° C. For example, by way of illustration and without limiting the scope of the invention, the materials for manufacturing the components of the device belong to the following group: stainless steel, copper and copper alloys, titanium and titanium alloys, aluminum and aluminum alloys, etc. The sensors and the micropositioners also have to be suitable for their use in a vacuum. The design of the device allows quickly removing the gases from the inside thereof, which allows its use in an ultra-high vacuum.

The invention claimed is:

1. A measurement device for measuring the force applied by a contact member on the surface of a sample, comprising a vacuum or controlled atmosphere chamber in which there are housed the sample and the contact member, mechanical means for transmitting the force exerted by the contact member in the form of the displacement of at least one flexible member and at least one sensor suitable for measuring said displacement, characterized in that it comprises at least one motor-driven linear micropositioner incorporated inside the vacuum or controlled atmosphere chamber for positioning a respective sensor and further comprising a control system for the micropositioner or the micropositioners located outside the vacuum or controlled atmosphere chamber for remotely controlling the sensor position relative to the flexible member.

2. The device according to claim 1, further comprising a microactuator capable of operating the micropositioner and the latter is located in linear guides.

3. The device according to claim 1, characterized in that it is adapted to measure at least one force that is tangential and/or normal to the surface.

4. The device according to claim 1, wherein the sensor is an optical-type sensor.

\* \* \* \* \*